United States Patent [19]
Labelle et al.

[11] Patent Number: 5,599,286
[45] Date of Patent: Feb. 4, 1997

[54] DEROTATING ORTHOTIC DEVICES FOR THE CORRECTION OF SCOLIOTIC DEFORMITIES

[75] Inventors: Hubert Labelle, Montréal; Jean Dansereau, Ste-Thérèse; Jacques A. de Guise, Montréal; Charles-Hilaire Rivard, St-Lambert; Martin LeBlanc, Montréal, all of Canada

[73] Assignee: Centre de Recherche de l'Hôpital Ste-Justine, Montréal, Canada

[21] Appl. No.: 171,169

[22] Filed: Dec. 22, 1993

[51] Int. Cl.$^6$ ........................................... A61F 5/00
[52] U.S. Cl. ................... 602/19; 128/875; 602/5
[58] Field of Search ............... 602/19, 4–6, 32, 602/36; 128/869, 874, 875

[56] References Cited

U.S. PATENT DOCUMENTS

| | | | |
|---|---|---|---|
| 1,803,556 | 5/1931 | Nugent | 602/19 |
| 3,095,875 | 7/1963 | Davidson et al. | |
| 3,220,407 | 11/1965 | Connelly | |
| 3,274,996 | 9/1966 | Jewett | |
| 3,282,264 | 11/1966 | Connelly | 602/19 |
| 3,543,748 | 12/1970 | Charters | 602/19 |
| 4,202,327 | 5/1980 | Glancy | |
| 4,230,101 | 10/1980 | Gold | 602/19 |
| 4,245,627 | 1/1981 | Mignard | |
| 4,285,336 | 8/1981 | Oebser et al. | |
| 4,658,807 | 4/1987 | Swain | |
| 4,688,558 | 8/1987 | Hooper, Jr. et al. | |
| 4,790,855 | 12/1988 | Jolly | 623/32 |
| 5,007,412 | 4/1991 | DeWall | 602/19 |
| 5,012,798 | 5/1991 | Graf et al. | |
| 5,205,815 | 4/1993 | Saunders | 602/19 |
| 5,256,135 | 10/1993 | Avihod | 602/19 |

FOREIGN PATENT DOCUMENTS

| | | |
|---|---|---|
| 1295901 | 2/1992 | Canada |
| 1299951 | 5/1992 | Canada |
| 2515028 | 4/1983 | France ................ 602/19 |
| 2000089 | 9/1993 | Russian Federation ......... 602/19 |
| 1725876 | 4/1992 | U.S.S.R. ......... 602/19 |

OTHER PUBLICATIONS

"Orthotic Treatment of Pediatric Spinal Disorders and Diseases", written by Labelle and Dansereau in Spine: State of the Art Reviews, vol. 4, No. 1, Jan. 1990, pp. 239–251.
"Indication de la gymnastique, des procédés orthopédiques et de la chirurgie dans les scolioses idiopathiques" written by Faucon et al in the Gazette Médicale de France, No. 3, Mar. 10, 1965 pp. 2–11.

(List continued on next page.)

*Primary Examiner*—Linda C. Dvorak
*Attorney, Agent, or Firm*—Swabey Ogilvy Renault

[57] ABSTRACT

A series of ortheses for the treatment of scoliotic deformities are each adapted for obliquely applying dynamic derotational forces on the thorax and lumbar spine of the user in opposite directions combined with a kyphosing action on the thorax and a lordosing action on the lumbar spine. The orthoses are designed in order that the correcting forces can be applied on the user's trunk with various degree of mechanical force while allowing for complete or partial mobility of the trunk. The various orthoses can treat small, moderate and substantially severe deformities which are supple or rigid. A supple orthosis for small and supple curves comprises a thoracic garment encircling the upper thorax, short pants to provide a grip around the pelvic girdle and the upper thighs, and upper and lower semi-elastic straps having supple thoracic and lumbar pads, respectively, attached respectively to the garment and the pants. The straps which connect the pads encircle obliquely the trunk for exerting the derotational forces and the kyphosing and lordosing actions. For moderate and supple curves, semi-rigid thoracic, lumbar and pelvic pads are incorporated in the orthosis. For rigid curves, the orthosis comprises a supple plastic shell encircling the pelvic girdle, a vertical member extending posteriorly and upward from the shell and comprising thoracic and lumbar pads. Semi-elastic strap means extend anteriorly between the pads while encircling obliquely the trunk. The vertical member can be integral with the shell or, for more rigidity, can consist of metallic member attached to the shell.

20 Claims, 4 Drawing Sheets

OTHER PUBLICATIONS

"Treatment of Idiopathic Scoliosis with the Wilmington Brace" written by Bassett et al. in The Journal of Bone and Joint Surgery, Incorporated, 68A, No. 4, Apr. 1986, pp. 602–605.

Miami TLSO in the Management of Scoliosis: Preliminary Results in 100 Cases written by McCollough, III, et al. in the "Journal of Pediatric Orthopedics", vol. 1. No. 2, 1981, pp. 141–152.

"The Thoracic Suspension Orthosis" written by Drennan et al in the Clinical Orthopaedics and Related Research, No. 139, Mar.–Apr. 1979, pp. 33–39.

"The Boston Brace System for the Treatment of Low Thoracic and Lumbar Scoliosis by the Use of a Girdle Without Superstructure" by Watts et al in Clinical Orthopaedics and Related Research No. 126, Jul.–Aug. 1977, pp. 87–92.

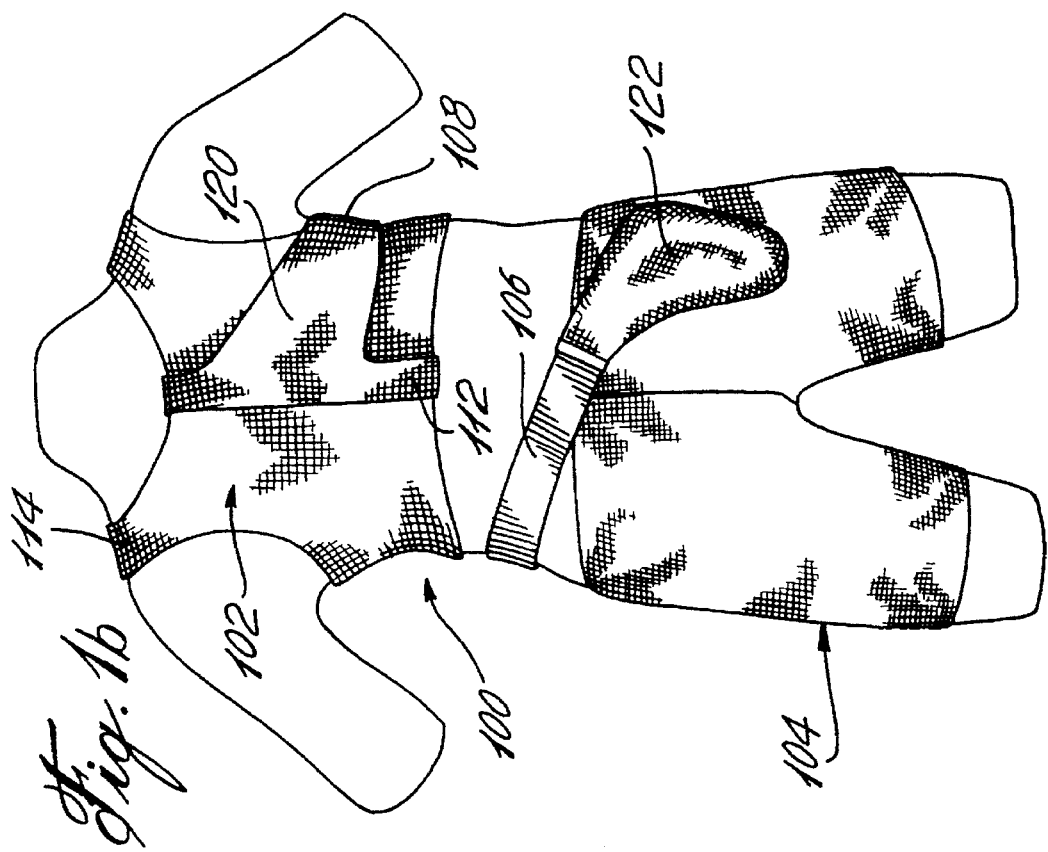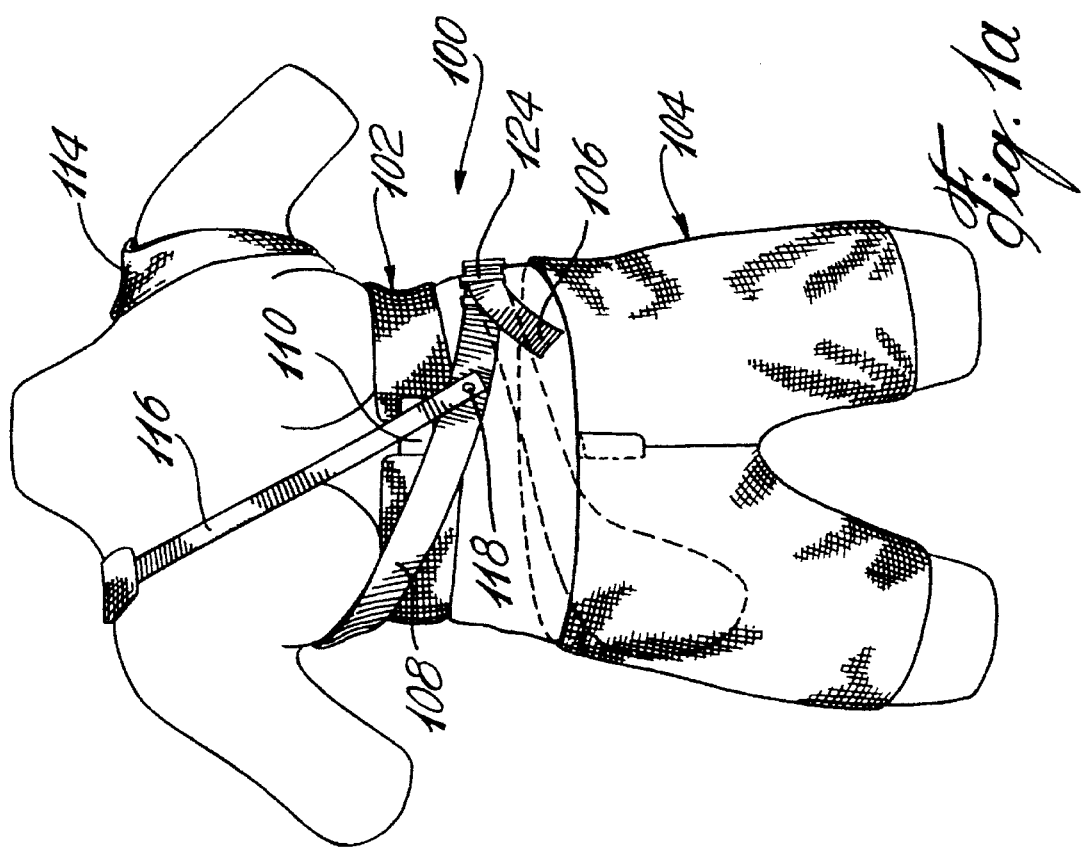

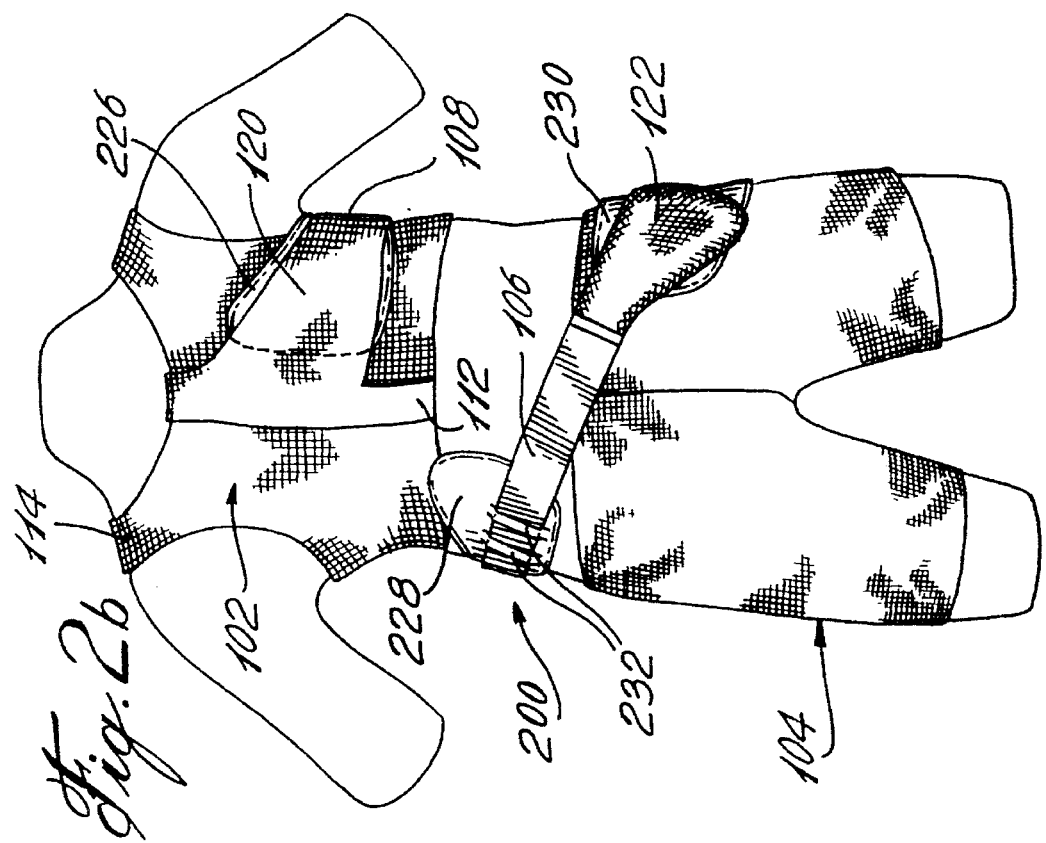
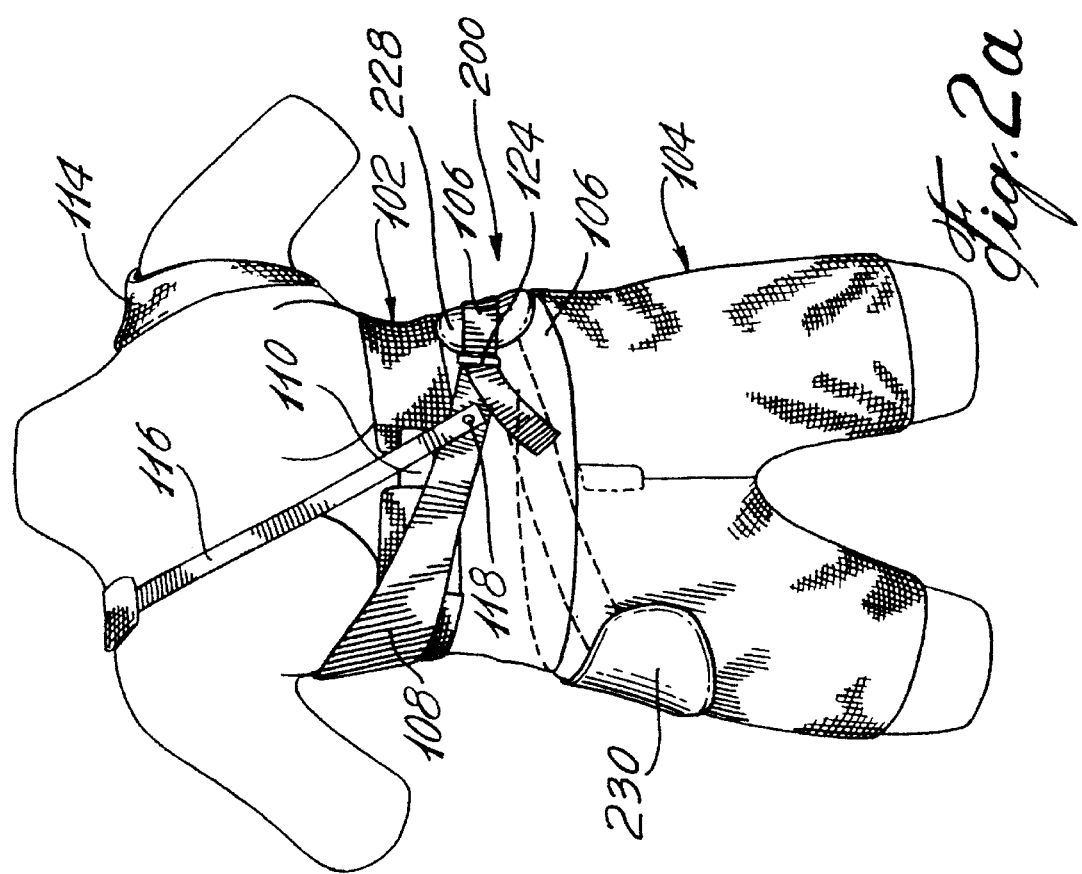

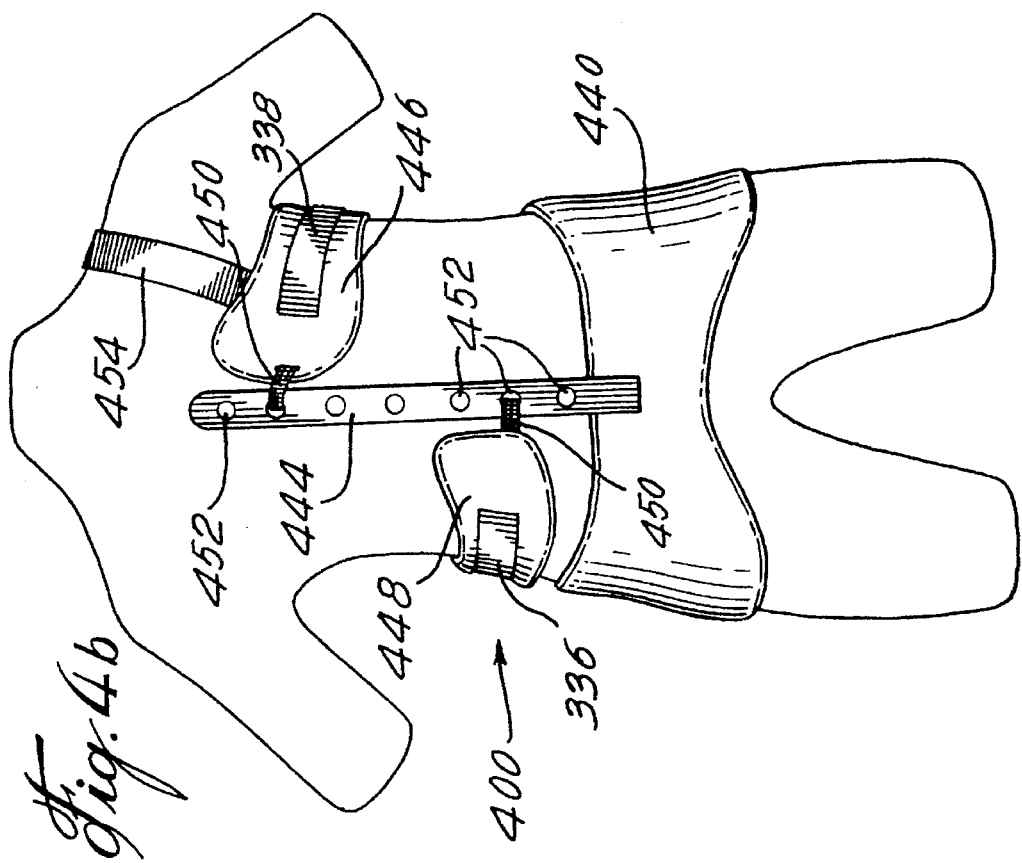
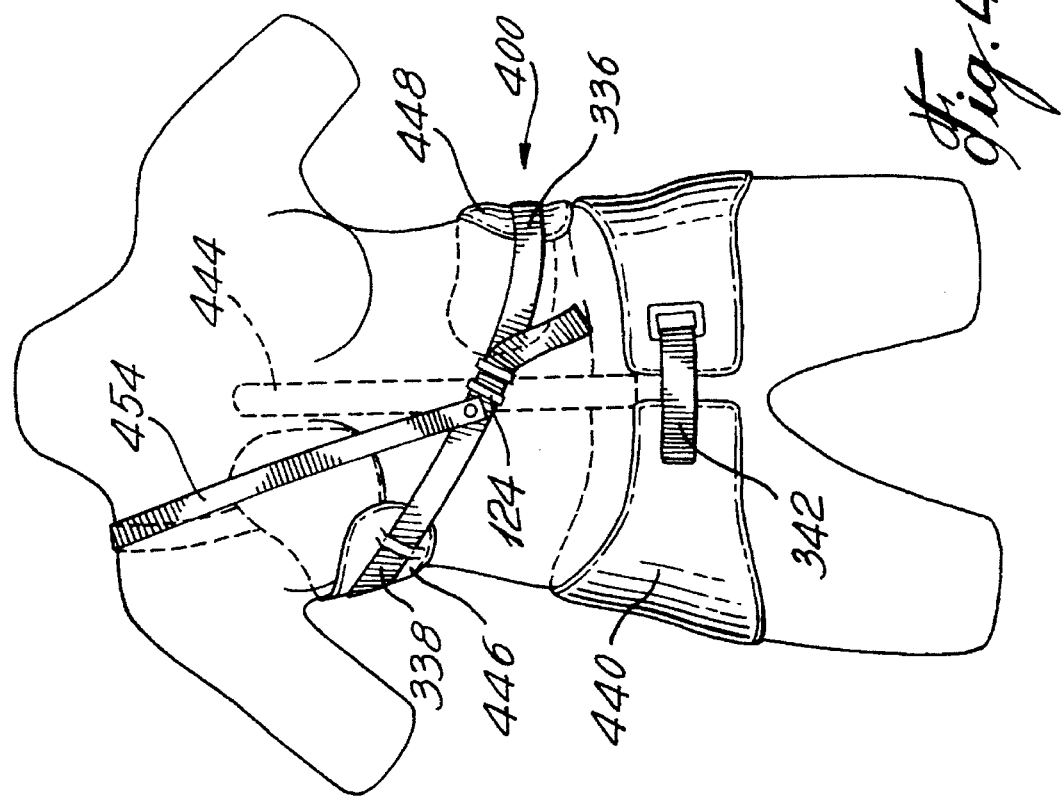

DEROTATING ORTHOTIC DEVICES FOR THE CORRECTION OF SCOLIOTIC DEFORMITIES

BACKGROUND OF THE INVENTION

1. Field of the Invention

The present invention relates to the non operative or orthotic treatment of scoliotic deformities and, more specifically, relates to a series of different orthoses that provide active corrective forces of derotation associated with kyphosing and/or lordosing forces on the trunk to provide a three dimensional (3-D) correction of scoliotic deformities, while still allowing complete or partial mobility of the trunk.

2. Description of the Prior Art

Scoliosis is a complex 3-D deformation of the trunk, spine and rib cage which involves "twisting" or rotation of the spine and rib cage in the transverse plane as well as lateral deviation of trunk in the frontal plane and usually a decrease of the normal curves in the sagittal plane. The most prevalent type is idiopathic scoliosis which affects 2 to 3% of the adolescent population. The harmful effects of spinal deformities have been recognized since antiquity, and although orthoses have been used in the treatment of scoliosis for centuries, an effective and widely recognized nonoperative method of treatment appeared only in 1945 with the advent of the Milwaukee brace, a description of which appears in the article entitled "Orthotic Treatment of Pediatric Spinal Disorders and Diseases" written by Labelle and Dansereau in "Spine: State of the Art Reviews", Vol. 4, No. 1, January 1990, pages 239–251. Orthotic management of spinal deformities is, therefore, a relatively new science still in evolution, explaining the rather large number of designs and materials that have appeared since the late 1960s.

An orthosis is an external orthopedic appliance used to control motion of body segments. The ideal orthosis for a spinal deformity should be able to restore the spine and rib cage to its normal alignment at the end of treatment. It should be lightweight, allow normal activities, be socially acceptable for the patient, and should not interfere with normal growth and development. These goals have not yet been fully achieved.

Before considering current orthoses in more detail, some general observations that apply to all braces need further discussion and should be kept in mind.

At present, there is no clear scientific proof of the validity of brace treatment, but there is strong clinical evidence to support it. Many publications have reported definite, positive, short- and long-term effects of bracing in idiopathic scoliosis, but they are retrospective case series without concurrent controls and are subject to many biases and methodological flaws.

The reported effects of bracing are remarkably similar in the literature. A curve improvement of 30 to 50% can usually be expected during brace wear, followed by a progressive loss of correction during weaning, with an eventual return to the prebrace measurement at follow-up. Success of brace treatment is thus limited to arrest of progression.

Braces work by the external application of a physical force at various locations on the thorax, spine, or pelvic girdle, and/or by active stimulation of corrective muscle contraction. The exact mode of action is not clearly understood, and the effect of bracing in the transverse and sagittal planes is poorly documented.

The usual indications for orthotic prescription include moderate curves between 20° to 40° in the skeletally immature. Braces have been usually worn on a full-time basis for periods varying from months to years, until skeletal maturity is reached, based on the premise that further progression will not occur at the end of growth.

There is no scientific proof or clinical evidence to support the use of physical therapy, intermittent traction, exercise, or manipulation as independently useful measures in the non-operative treatment of spinal deformities.

The nomenclature developed in 1973 by the Task Force on Standardization of Orthotics Terminology is now widely accepted and is based on the joints or segments of the body encompassed. Two categories are of importance: CTLSO (cervical- thoracic-lumbar-sacral orthosis) and TLSO (thoracic- lumbar-sacral orthosis).

As progressive scoliotic deformities in adolescents may require treatment by a brace, various types of braces have been proposed in the past 50 years. In North America, one of the earliest type, still in use today, is the aforementioned Milwaukee brace (CTLSO) which consists of a molded plastic pelvic girdle, two metal uprights in the back and one upright in the front, all of which are adjustable. A neck ring with a throat pad is connected to the cephalic portion of the uprights. The brace works mostly by passive corrective lateral forces and longitudinal distraction by the neck ring, and is bulky and visible under the clothes so that compliance in the adolescent population is fairly low.

The Milwaukee brace was replaced in the early '70s by the Boston brace system (TLSO) which is described in the aforementioned Labelle et al. article and also in "Indications de la gymnastique, des procédés orthopédiques et de la chirurgie dans les scolioses idiopathiques" written by Faucon et al. in the "Gazette Médicale de France", No. 3, Mar. 10 1965, pages 2–11. The Boston brace characterized by a series of prefabricated polypropylene molds which open from the back and are designed to firmly grip the pelvis and thorax to provide correction by passive forces with a three-point pressure principle and by the contact fit of the brace.

Many other orthotic devices (TLSO) made of rigid thermoplastic materials (such as the DuPont jacket, the Miami TLSO, the Newington brace, etc.) have also been designed as similar rigid torso-enveloping shells, but differ from the Boston brace in that they are usually custom fabricated from a positive mold of the patient taken supine on a traction table and that they work mostly by total trunk contact passive forces. Descriptions of the Dupont jacket appear in the aforementioned Labelle et al. reference and also in the article entitled "Treatment of Idiopathic Scoliosis with the Wilmington Brace" written by Bassett et al. in "The Journal of Bone and Joint Surgery, Incorporated", 68A, No. 4, April 1986, pages 602–605. The Miami TLSO is described in the aforementioned Labelle et al. article and also in "Miami TLSO in the Management of Scoliosis: Preliminary Results in 100 Cases" written by McCollough, III, et al. in the "Journal of Pediatric Orthopedics", Vol. 1, No. 2, 1981, pages 141–152. The Newington brace is also described in the Labelle et al. reference as well as in "The Thoracic Suspension Orthosis" written by Drennan et al. in the "Clinical Orthopaedics and Related Research", No. 139, March-April 1979, pages 33–39.

A dynamic orthotic device (U.S. Pat. No. 4,202,327 issued on May 13, 1980 to Glancy) has been claimed by Glancy to correct scoliotic deformities by means of a rigid torso enveloping shell with precut shell segments hinged to the rigid shell at one end and connected by an elastic strap to the rigid shell at the other end to provide a dynamic horizontal transverse pressure in a scoliotic deformity.

More recently, the Charleston bending brace (U.S. Pat. No. 4,688,558 issued on Aug. 25, 1987 to Hooper, Jr. et al.) has been introduced: it consists also of a rigid custom fabricated total contact plastic jacket but it is molded supine with a straight lateral unbending force at the apex of the scoliotic curve. It is designed for night time bracing only, contrary to previous orthoses.

In Europe, the Lyonese brace (TLSO) is a rigid three and four valve orthosis made of custom fitted "plexi-dur" and aluminum materials and works by three or four point pressures applied laterally to the scoliotic deformities. The Lyonese brace is mentioned in the aforementioned Labelle et al. and McCollough articles. From this brace, a lighter version of the Lyonese brace called the Olympe has been recently developed: it is claimed to combine part of the Lyonese brace for support and rigidity, and part of the elastic brace of "Corset Toilé de St-Étienne" to make it lighter and more easily tolerable.

Another recent development is the 3-D brace (U.S. Pat. No. 5,012,798 issued on May 7, 1991 to Graf et al.), a rigid orthosis which consists of a molded plastic pelvic girdle connected to two plastic hands by two elastically semi-rigid lateral supports that can be put out of shape. 3-D correction is said to be achieved during the inspiratory phase of the respiratory cycle when the brace forces reduction by opposing the expansion of the thoracic cage.

All the aforementioned braces are partly or completely rigid thereby inhibiting completely the normal movements of the thoracic and lumbar spine in flexion, extension and lateral bending. These braces are also bulky and for these reasons used mostly for moderate or severe deformities. Furthermore, with all current orthoses, there is only one basic design available to correct any degree of curve severity of stiffness even if there are mild, moderate or severe curves that are of varying degree of stiffness.

SUMMARY OF THE INVENTION

It is therefore an aim of the present invention to provide orthotic devices for the treatment of scoliotic deformities which allow partial or complete trunk mobility contrary to current orthoses.

It is also an aim of the present invention to provide such an orthotic device which provides active correcting derotational forces rather than passive correcting forces.

It is a further aim of the present invention to provide such an orthotic device which provides correction by combining the forces of transverse derotation on the thorax coupled with a kyphosing action on the thoracic spine while providing forces of transverse derotation coupled with a lordosing action on the lumbar spine.

It is a still further aim of the present invention to provide a system of orthotic devices for the treatment of scoliotic deformities which is modular in order to allow various degrees and locations of mechanical action, while preserving some normal motion of the trunk, in order to account for varying curve severities and stiffnesses.

Therefore, in accordance with the present invention, there is provided an orthotic device made of supple material for the treatment of scoliotic deformities comprising an upper thoracic garment means adapted to encircle the upper thorax of a user, a pair of pant means adapted to provide a grip around the pelvic girdle and the upper thighs of the user, and semi-elastic strap means having supple thoracic and lumbar pad means, the thoracic and lumbar pad means being attached, in use, respectively to the garment means and the pant means, the strap means being adapted to connect the pad means, the strap means intermediate the pad means being adapted to encircle obliquely at least partly the trunk of the user for exerting derotational forces on the rib cage, thoracic spine and lumbar spine of the user in opposite directions as well as kyphosing and lordosing forces respectively on the upper thorax and on the lumbar spine of the user.

For substantially small and supple curves, the garment means is made of a stretchy material and of cotton (or similar material) and is adapted to leave the user's arms free, the pant means being made of a stretchy material covering the pelvic girdle and substantially the upper two-thirds of the user's thighs, the pad means being made of cotton (or similar material). Preferably, the strap means comprise upper and lower straps adapted to be attached with a desired force anteriorly of the user.

For moderate but supple curves, there are provided semi-rigid thoracic, lumbar and pelvic pad means incorporated at appropriate locations on the orthotic device. Preferably, the pad means are made of a plastic semi-rigid material with an interior padding, such as a foam padding. Also, the semi-rigid thoracic and pelvic pad means are substantially provided on the orthotic device adjacent the supple thoracic and lumbar pad means, the semi-rigid lumbar pad means being located at the strap means intermediate the supple thoracic and lumbar pad means. Further, the semi-rigid lumbar pad means is substantially fitted around the postero-lateral flank of the user, covering the apex of the lumbar deformity.

Also in accordance with the present invention, there is provided an orthotic device for the treatment of scoliotic deformities comprising a supple shell means adapted to encircle the pelvic girdle of a user, a substantially vertical member means extending posteriorly and upward from the shell means and comprising thoracic and lumbar pad means, semi-elastic strap means adapted to extend anteriorly between the pad means and to encircle obliquely at least partly the user's trunk for exerting derotational forces on the thorax and lumbar spine of the user in opposite directions as well as kyphosing and lordosing forces respectively on the upper thorax and on the lumbar spine of the user.

For moderate but rigid curves, the member means is integral with the shell means and is substantially supple, the pad means extending integrally from the member means, the strap means comprising upper and lower straps adapted to be attached with a desired force anteriorly of the user. Preferably, the shell means, the member means and the pad means are all made of a supple plastic material.

For rigid and substantially severe curves, the member means is made from a substantially rigid material, means being provided for attaching the pad means to the member means. Preferably, the shell means is made from a plastic material and the member means is made from a metallic material. Also, the orthotic device can provide a kyphosing force by way of a shoulder strap means extending posteriorly from the thoracic pad means, over the user's shoulder and anteriorly for connection to the semi-elastic strap means.

Further in accordance with the present invention, there is provided a method of treatment of scoliotic deformities by obliquely applying dynamic derotational forces on the thorax and lumbar spine of the user in opposite directions combined with a kyphosing action on the thorax and a lordosing action on the lumbar spine.

More particularly, the correcting forces are applied on the user's trunk with various degree of mechanical force while allowing for complete or partial mobility of the trunk. Therefore, the present method is adapted for treating supple, rigid, small, moderate and substantially severe deformities.

The present invention differs from the prior art in that it consists of a system of four orthopedic appliances providing correction of the deformity through semi-elastic straps applied obliquely on the trunk and providing a mechanism of derotation and kyphosing action on the rib cage and thoracic spine as well as derotation and lordosing action on the lumbar spine, with a view of restoring the normal contours of the trunk.

The system has various degrees of rigidity in order to exert these above-described forces obliquely on the trunk with various degrees of strength for providing treatment of various severities and stiffnesses of scoliotic deformities while still maintaining complete or partial trunk mobility. Small and supple curves are treated with a first orthotic device in accordance with the present invention which permits realignment of the scoliotic deformity without interfering with normal trunk and spine mobility. Moderate and supple curves are treated with a second orthotic device also in accordance with the present invention which provides a stronger mechanical action while still preserving near normal motion of the trunk. Moderate but more rigid curves are treated with a third orthotic device also in accordance with the present invention which provides greater mechanical correction while still maintaining partial mobility of the trunk. Finally, rigid and moderate or severe curves are treated with a fourth orthotic device also in accordance with the present invention which provides strong mechanical action while allowing, however, less mobility.

BRIEF DESCRIPTION OF THE DRAWINGS

Having thus generally described the nature of the invention, reference will now be made to the accompanying drawings, showing by way of illustration a preferred embodiment thereof, and in which:

FIGS. 1a and 1b are front and rear elevation views, respectively, of a first orthotic device in accordance with the present invention which is shown being worn on a human torso;

FIGS. 2a and 2b are front and rear elevation views, respectively, of a second orthotic device in accordance with the present invention which is shown being worn on a human torso;

FIGS. 4a and 4b are front and rear elevation views, respectively, of a fourth orthotic device in accordance with the present invention which is shown being worn on a human torso.

DESCRIPTION OF THE PREFERRED EMBODIMENTS

Figure 3B:
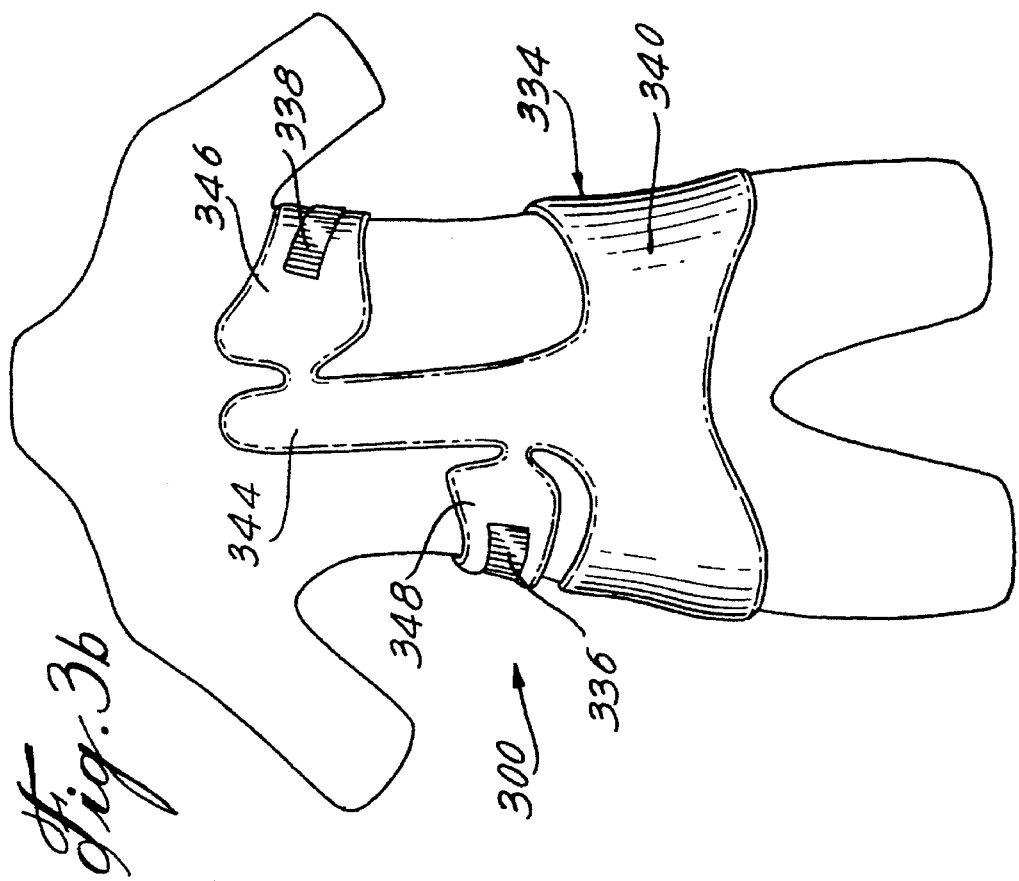
FIGS. 3a and 3b are front and rear elevation views, respectively, of a third orthotic device in accordance with the present invention which is shown being worn on a human torso.

1—*Derotating Supple Orthosis* (FIGS. 1a and 1b)

In a first embodiment in accordance with the present invention, a first orthosis 100 intended for treating small and supple curves is made entirely of supple material thereby allowing for nearly normal mobility of the spine while providing the previously mentioned correcting forces on the scoliotic deformity.

The first orthosis 100 comprises three basic components: an upper thoracic "body jacket" 102, a lower short pant 104 and a set of connecting semi-elastic straps 106 and 108. In its actual state, the upper "body jacket" 102 is made of stretchable material and cotton ("DACRON", i.e. a polyester fiber made in filament and staple form and having great resiliency), and is fastened in front under the breast line by a "Velcro" (i.e. a hook and loop fastener) attachment 110. In the back, the stretchable jacket 102 covers the thorax from the lower neck to the lower ribs, leaving the arms free. In the central posterior part, there is provided a vertical longitudinal cotton "(Dacron)" reinforcement band 112 which is 2 to 3 inches wide. To this reinforcement band 112 is secured a "derotational" semi-elastic strap, described in details hereinbelow. In the front, there is a shoulder strap 114 on the left shoulder which attaches laterally and inferiorly to the lateral side of the jacket 102. From posterior to anterior on the right shoulder, the jacket 102 is connected to another semi-elastic strap 116 which passes obliquely in front of the thorax between the breasts to attach by an adjustable clip 118 to the "derotational" semi-elastic strap as it passes in front of the thoracoabdominal junction.

This thoracic soft tissue body jacket 102 is prefabricated in different sizes in order to accommodate most children and adolescents sizes or can be custom fabricated from a set of anthropometric measurements for subjects of unusual size or body configuration.

The lower component of the supple tissue orthosis 100 is the pair of "stretch" pants 104 available in various sizes to accommodate most children and adolescents. They can also be custom fabricated from a set of anthropometric measurements for subjects who cannot be accommodated with prefabricated sizes. These pants 104 are tightly adjusted on the pelvis and down to the mid thigh by the stretching of the tissue in order to provide a large surface contact on the lower part of the trunk. To this lower part are attached a derotational semi-elastic strap 106 and pad 122, on the posterior right buttock.

The third element of the supple tissue orthosis 100 is the pair of semi-elastic straps 106 and 108 which provide dynamic correcting forces on the scoliotic deformity by connecting the upper body jacket 102 to the lower body short pants 104. In their current design, these semi-elastic straps 106 and 108 are made of two components: triangular cotton pads 120 and 122 which are sewn respectively at one extremity of the upper 102 or lower 104 portion of the orthosis 100, and the semi-elastic tissue bands 108 and 106 (3" wide and ⅛" thick in their current state) which are sewn to the other extremity of the cotton pads 120 and 122, respectively.

The combination of the upper strap and pad 108 and 120 attaches posteriorly on the cotton reinforcement band 112 and passes obliquely downward to the right over the ribs situated at the apex of the scoliotic deformity, usually the eighth and ninth rib. The strap 108 continues obliquely and downward around the thorax and over the abdomen in front where the anterior shoulder strap 116 connects. The lower derotational strap made of the lower strap and pad 106 and 122, respectively, is sewn and attached to the area of the right buttock and travels obliquely and upward toward the left flank to pass over the apex of the lumbar scoliotic deformity, usually the second and third lumbar vertebrae. It travels upward around to connect in front of the abdomen to the upper strap 108. The connection between the two straps 106 and 108 in its current design is obtained via a buckle 124 with an adjustable tension by manually pulling on one extremity of the straps 106 and 108. This tension is adjusted in order to provide dynamic correcting forces on the thoracic and lumbar scoliotic deformity.

The two upper semi-elastic straps 108 and 116 provide derotation of the right thoracic rib hump and a kyphosing force on the thoracic spine and thorax. The lower semi-elastic strap 106 provides derotation and a lordosing force in the opposite direction on the apex of the left lumbar spinal deformity- The correction forces are active by virtue of the elastic recoil and since there are no rigid parts, the subject has to counteract these forces to maintain his trunk equilibrium, thus providing active correction of the deformity.

The first orthosis 100 described in FIGS. 1a and 1b and discussed hereinabove pertains to a standard right thoracic and left lumbar scoliotic curve. This basic configuration of the supple tissue orthosis can be altered to accommodate other scoliotic patterns by changing the position and insertion of the straps. For example, the configuration illustrated in FIGS. 1a and 1b can be reversed in a mirror image for left thoracic and right lumbar curves. For simple right thoracic or thoracolumbar curves, the upper derotational strap 108, 120 is sewn so as to travel over the ribs at the apex of the scoliotic curve but the lower derotational strap 106 is sewn on the left side of the pants 104 in order to provide corrective forces on the thorax only and not on the lumbar spine. In the same manner, for single lumbar curve patterns, the upper derotational strap 108,120 is sewn antero-laterally on the upper section 102 of the orthosis 100 rather than posterolaterally. In cases where a kyphosis action on the thorax is not deemed necessary, the anterior kyphosing strap 116 can be replaced by a shoulder strap. These configurations are recommended for standard scoliotic deformities, but the modularity of the orthosis 100 allows the treating physician to change these configurations to accommodate different scoliotic deformities.

2—*Derotating Semi-Supple Orthosis* (FIGS. 2a and 2b)

Also in accordance with the present invention, a second orthosis 200 intended for treating moderate and supple curves incorporates the same basic design of the supple tissue orthosis 100 described hereinbefore to which upper, intermediate and lower semi-rigid pads 226, 228 and 230, respectively, are incorporated in order to apply the three-point pressure principle to the upper and lower derotational straps 108,120 and 106,122, respectively, so that greater corrective forces can be applied. These semi-rigid pads 226, 228 and 230 also provide a larger surface contact area under these derotational straps thereby distributing the pressure of the corrective forces over a larger surface area.

In their present state, the semi-rigid pads 226, 228 and 230 are made of a polymer having a thickness of approximately ⅛ inch to ¼ inch, such as polypropylene, with an interior foam padding. The semi-rigid pads are prefabricated in different sizes to accommodate most deformities but can also be custom made from a mold of a subject whose deformity is not adapted to standard fits.

There are three different pads that can be used alone or in any combination according to the clinical situation: the upper thoracic pad 226, the intermediate lumbar pad 228 and the lower pelvic pad 230. The thoracic pad 226 has an "L" or semi-circular shape that covers the posterior and lateral aspects of the thoracic cage over three or four ribs, extending anteriorly to the antero-lateral aspect of the thorax, in order to fit underneath the upper semi-elastic derotational strap 108,120. The pad 226 is inserted in a cotton double lining or pouch sewn to the underside of the derotational strap 108, 120 at the appropriate location, allowing it to remain stable between the skin of the patient and the soft tissue orthosis.

The lumbar pad 228 has a semi-circular bean shape in order to fit around the postero-lateral flank, covering the apex of the lumbar deformity. This pad 228 is covered by a soft tissue lining and is inserted over the skin and underneath the lower semi-elastic derotational strap 106. The lumbar pad 228 is connected to the strap 106 by two tissue bands or belt loops 232 that allow the lumbar pad 228 to slide longitudinally under the strap 106 for proper location of the pad 228 on the patient.

Finally, the pelvic pad 230 has a semicircular or U shape designed to fit over the iliac crest on the lateral side extending downward above the greater trochanter, anteriorly up to the anterior superior iliac spine and posteriorly over half of the buttock area. This pad 230 provides a firm grip on one side of the pelvis and is fitted between the triangular cotton pad 122 of the lower elastic derotational strap 106, 122 and is incorporated in the stretch pants 104.

The example shown in FIGS. 2a and 2b relates to a standard right thoracic and left lumbar curve. As for the supple tissue orthosis 100, this orthosis configuration 200 can be modified to accommodate other patterns of scoliotic deformities. For example, in a simple right thoracic curve, the lower derotational strap 106,122 and the pelvic pad 230 are located on the left side of the patient. For a right thoracolumbar curve pattern, the same configuration is used but the upper derotational strap 108,120 is applied over the lower part of the thorax (eleventh or twelfth rib).

If a kyphosing force on the thorax is not necessary, the anterior kyphosing strap 116 is replaced by a shoulder strap. For left thoracic and right lumbar curves, a mirror image of the orthosis 200 is used. For more unusual patterns, a different and customized configuration may be used by a clinician using the same basic components of the second semi-supple orthosis 200.

Figure 3A:
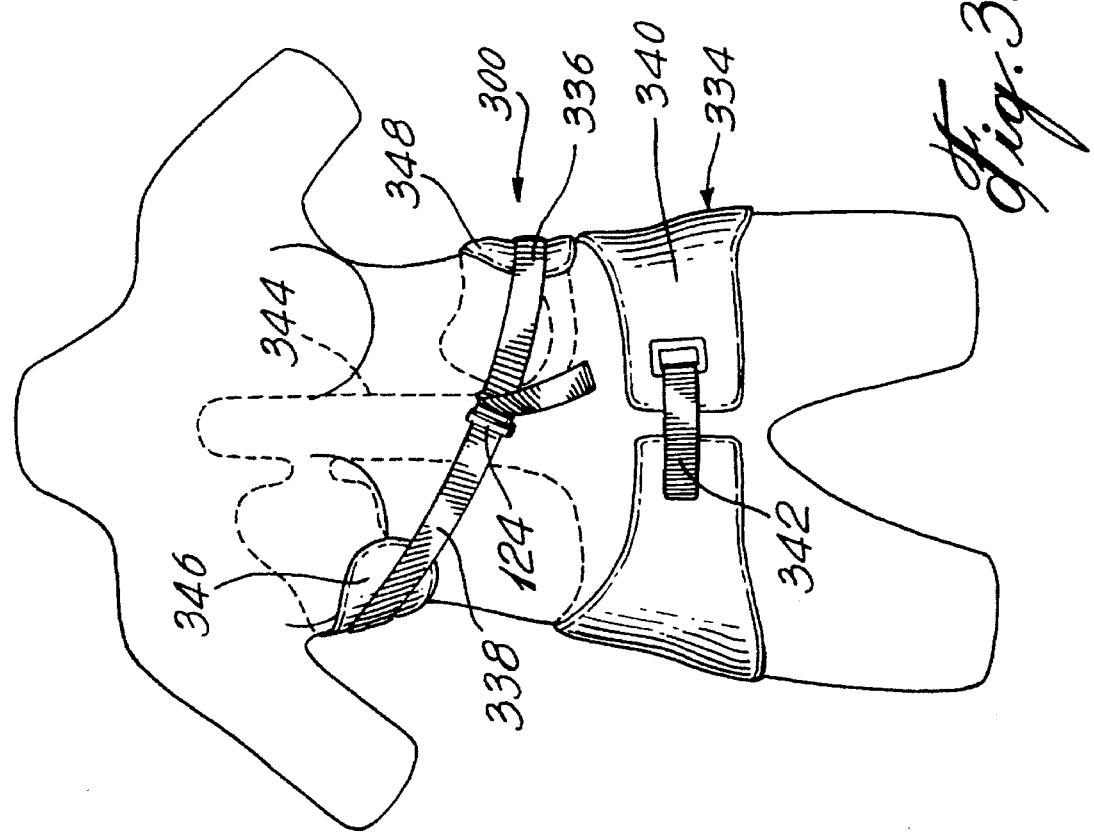

3—*Derotating Plastic Orthosis* (FIGS. 3a and 3b)

Further in accordance with the present invention, a third orthosis 300 has been designed with the same principles of correction but is used for treating moderate but more rigid scoliotic deformities. It comprises two basic units: a plastic polymer semi-rigid shell 334 and a set of semi-elastic derotational straps 336 and 338. It provides stronger support to apply corrective forces while still allowing some motion of the thorax and spine.

The polymer shell 334 is a single piece polymer unit of approximately ¹⁄₁₆" thick polypropylene consisting of a pelvic girdle 340 encircling the human pelvic girdle with a front entry secured by a VELCRO attachment 342. The pelvic girdle 340 grips the pelvis firmly over the iliac crests down to above the greater trochanter on the lateral side, over the pubis in the front, and down to half the buttocks posteriorly. Extending superiorly from the center of the posterior pelvic girdle 340 is a central mast 344 which follows the center of the spine up to the upper thoracic area. This mast 344 provides a semi-rigid link to which are attached thoracic and lumbar pads 346 and 348, respectively. These pads 346 and 348 have the same configuration as the thoracic and lumbar pads 226 and 228 of the semi-supple tissue orthosis 200. The polymer shell 334 is available in prefabricated sizes or can be custom fabricated from a cast mold of the trunk for subjects with non standard deformities.

The pair of semi-elastic derotational straps 336 and 338 provide a similar corrective action as the straps 106 and 108 on the supple and semi-supple tissue orthoses 100 and 200, respectively. The upper derotational strap 338 is a 3"×⅛" (approximately) semi-elastic strap sewn to the anterior extremity of the thoracic pad 346. The lower derotational strap 336 is also a 3"×⅛" (approximately) semi-elastic strap sewn to the anterior extremity of the lumbar pad 348. These two straps 336 and 338 can be attached together anteriorly by a buckle 124 which allows the tension to be adjusted by manual pull on one of the straps 336 and 338. This tension is adjusted to provide the required dynamic correcting forces on the thoracic and lumbar deformities.

If required, a tissue shoulder strap around the left shoulder which is sewn to the upper extremity of the plastic mast 344 can be added to provide further support. If required, an upper right thoracic kyphosing strap can also be attached to the upper posterior portion of the thoracic pad 346 to provide a kyphosing action on the thorax. This kyphosing strap has the same direction and configuration as the strap 116 described in the previous two orthoses 100 and 200.

The configuration illustrated in FIGS. 3a and 3b is for a standard right thoracic and left lumbar curve pattern. As discussed for the previous orthoses 100 and 200, the configuration can be changed to treat other curve patterns following the same guidelines already discussed for the supple and semi-supple tissue orthoses Mobility of the trunk and spine is only partly inhibited by the design of the third plastic orthosis 300 by virtue of the thickness of the polypropylene shell which is deformable. 4—*Rigid Derotation Orthosis* (FIGS. 4a and 4b)

Still further in accordance with the present invention, a fourth orthosis 400 has been designed on the same basic principles of correction but is more rigid and thus indicated for moderate to severe and rigid curves. A stronger mechanical action is obtained but normal mobility of the trunk is more restricted though less than with other currently available orthotic devices which do not allow any motion in flexion, rotation or lateral bending. The basic design of the fourth orthosis 400 is the same as for the third plastic orthosis 300 except that the posterior central plastic polymer semi-rigid mast 344 of the third orthosis 300 is replaced by a metallic aluminum mast 444 and the polymer used for the pelvic girdle 440 and thoracic and lumbar pads 446 and 448, respectively, is thicker (⅛"), thus providing a more rigid construction on which a stronger mechanical action can be obtained with the upper and lower derotational straps 338 and 336, respectively. In its present state, the rigid orthosis 400 is thus composed of the plastic pelvic girdle 440, the aluminum posterior mast 444 fixed to the girdle 440 by rivets, the lumbar pad 448 and the thoracic pad 446 both fixed to the mast 444 by a flexible cotton rope 450 threaded in holes 452 of the mast 444, and the pair of derotational semi-elastic strap 336 and 338 sewn at one end to respective ones of the pads 446 and 448 and attached together at the other extremity by an adjustable buckle 124. If a kyphosing action on the thorax is needed, a kyphosing semi-elastic strap 454 can be added as in all other components of the system, that is all the other orthoses 100, 200 and 300.

Once again the configuration is for a standard right thoracic and left lumbar curve pattern. This configuration can be altered in the same manner as suggested previously for other components in order to accommodate other curve patterns.

I claim:

1. An orthotic device made of supple material for the treatment of scoliotic deformities comprising an upper thoracic garment means adapted to encircle the upper thorax of a user, a pair of pant means adapted to provide a grip around the pelvic girdle and the upper thighs of the user, and semi-elastic strap means having supple thoracic and lumbar pad means, said thoracic and lumbar pad means being attached, in use, respectively to said garment means and said pant means, said strap means being adapted to connect said thoracic and lumbar pad means one to another, said strap means intermediate said pad means being adapted to encircle obliquely at least partly the trunk of the user for exerting derotational forces on the rib cage, thoracic spine and lumbar spine of the user in opposite directions as well as kyphosing and lordosing forces respectively on the upper thorax and on the lumbar spine of the user.

2. An orthotic device as defined in claim 1, wherein said garment means is made of a stretchy material and of cotton and is adapted to leave the user's arms free, wherein said pant means is made of a stretchy material adapted to cover the pelvic girdle and substantially the upper two-thirds of the user's thighs, and wherein said pad means are made of cotton, said orthotic device being intended for substantially small and supple curves.

3. An orthotic device as defined in claim 1, wherein said strap means comprise upper and lower straps adapted to be attached with a desired force anteriorly of the user.

4. An orthotic device as defined in claim 1, further comprising semi-rigid thoracic, lumbar and pelvic pad means for providing a semi-supple derotational orthotic device intended for moderate but supple curves.

5. An orthotic device as defined in claim 4, wherein said semi-rigid pad means are made of a plastic semi-rigid material with an interior padding.

6. An orthotic device as defined in claim 4, wherein said semi-rigid thoracic and pelvic pad means are substantially provided on said orthotic device adjacent said supple thoracic and lumbar pad means, said semi-rigid lumbar pad means being located at said strap means intermediate said supple thoracic and lumbar pad means.

7. An orthotic device as defined in claim 6, wherein said semi-rigid lumbar pad means is adapted to be substantially fitted around the postero-lateral flank of the user, and is thus adapted to cover the apex of the lumbar deformity.

8. An orthotic device for the treatment of scoliotic deformities comprising an upper thoracic attachment means adapted to be removably installed on a user substantially at an upper thorax thereof, a lower pelvic attachment means adapted to be removably installed on the user substantially at the pelvic girdle thereof, and elastic means adapted to be anchored at upper and lower parts thereof respectively to said upper and lower attachment means and to extend substantially obliquely intermediate said upper and lower attachment means in such a manner as to encircle at least part of the trunk of the user, whereby said elastic means exert derotational forces on the thoracic and lumbar spines of the user in opposite directions as well as kyphosing and lordosing forces respectively on the upper thorax and on the lumbar spine of the user.

9. An orthotic device as defined in claim 8, wherein said device is made of supple material, said upper attachment means comprising an upper thoracic garment means adapted to encircle the upper thorax of the user, said lower attachment means comprising a pair of pant means adapted to provide a grip around the pelvic girdle and the upper thighs of the user, said elastic means comprising semi-elastic strap means having supple thoracic and lumbar pad means, said thoracic and lumbar pad means being attached, in use, respectively to said garment means and said pant means with said strap means being adapted to interconnect said thoracic and lumbar pad means, said strap means intermediate said pad thoracic and lumbar means being adapted to obliquely encircle at least part of the trunk of the user.

10. An orthotic device as defined in claim 9, wherein said garment means is made of a stretchy material and of cotton, or similar material, and is adapted to leave the user's arms free, wherein said pant means is made of a stretchy material covering the pelvic girdle and substantially the upper two-thirds of the user's thighs, and wherein said thoracic and lumbar pad means are made of cotton, said orthotic device being intended for substantially small and supple curves.

11. An orthotic device as defined in claim 9, wherein said strap means comprise upper and lower straps adapted to be attached together with a desired force anteriorly of the user.

12. An orthotic device as defined in claim 9, further comprising semi-rigid thoracic, lumbar and pelvic pad means incorporated at appropriate locations on said orthotic device for providing a semi-supple derotational orthotic device intended for moderate but supple curves.

13. An orthotic device as defined in claim 12, wherein said semi-rigid pad means are made of a semi-rigid plastic material with an interior padding, such as a foam padding.

14. An orthotic device as defined in claim 12, wherein said semi-rigid thoracic and pelvic pad means are substantially provided on said orthotic device adjacent said supple thoracic and lumbar pad means, said semi-rigid lumbar pad means being located at said strap means intermediate said supple thoracic and lumbar pad means and being substantially fitted around the postero-lateral flank of the user, covering the apex of the lumbar deformity.

15. An orthotic device as defined in claim 8, wherein said lower attachment means comprise supple shell means adapted to encircle the pelvic girdle of the user and lumbar pad means depending from a lower end of a substantially vertical mast means extending posteriorly of the user and upwardly from said shell means, said upper attachment means comprising thoracic pad means depending from an upper end of said mast means, said elastic means comprising semi-elastic strap means adapted to extend anteriorly between said thoracic and lumbar pad means and to obliquely encircle at least part of the user's trunk.

16. An orthotic device as defined in claim 15, wherein said mast means is integral with said shell means and is substantially supple, said thoracic and lumbar pad means extending integrally from said mast means and on opposite sides thereof, and wherein said strap means comprise upper and lower straps adapted to be attached with a desired force anteriorly of the user, said orthotic device being intended for moderate but rigid curves.

17. An Orthotic device as defined in claim 16, wherein said shell means, said mast means and said thoracic and lumbar pad means are all made of a supple plastic material.

18. An orthotic device as defined in claim 15, wherein said mast means is made from a substantially rigid material, means being provided for attaching said thoracic and lumbar pad means to opposite sides of said mast means substantially at said upper and lower ends, said orthotic device being intended for rigid and substantially severe curves.

19. An orthotic device as defined in claim 18, wherein said shell means is made from a plastic material and said mast means is made from a metallic material.

20. An orthotic device as defined in claim 18, wherein said orthotic device provides a kyphosing force by way of a shoulder strap means extending posteriorly from said thoracic pad means, over a shoulder of the user and anteriorly for connection to said semi-elastic strap means.

* * * * *